United States Patent [19]
Perroz, Jr. et al.

[11] Patent Number: 5,826,577
[45] Date of Patent: Oct. 27, 1998

[54] BREATH GAS ANALYSIS MODULE

[75] Inventors: William J. Perroz, Jr., Parks Township; William P. Spohn, Gibsonia, both of Pa.

[73] Assignee: Bacharach, Inc., Pittsburgh, Pa.

[21] Appl. No.: 593,564

[22] Filed: Jan. 30, 1996

[51] Int. Cl.$^6$ ................................................ A61B 5/08
[52] U.S. Cl. ........................ 128/719; 128/716; 128/720; 128/721; 128/725
[58] Field of Search .................. 128/716, 719, 128/720, 721, 725, 727, 728

[56] References Cited

U.S. PATENT DOCUMENTS

| | | | |
|---|---|---|---|
| 1,474,904 | 11/1923 | Jones | 128/718 |
| 2,591,691 | 4/1952 | Forrester | 23/232 |
| 2,795,223 | 6/1957 | Stampe | 128/2 |
| 3,746,512 | 7/1973 | Kamei et al. | 23/232 E |
| 4,202,352 | 5/1980 | Osburn | 128/719 |
| 4,300,385 | 11/1981 | Albarda | 73/23 |
| 4,424,276 | 1/1984 | Clark et al. | 436/50 |
| 4,786,472 | 11/1988 | McConnell et al. | 422/61 |
| 4,941,476 | 7/1990 | Fisher | 128/719 |
| 5,018,395 | 5/1991 | Hickox et al. | 73/502 |
| 5,022,406 | 6/1991 | Tomlinson | 128/719 |
| 5,052,213 | 10/1991 | Stock | 73/23.3 |
| 5,067,492 | 11/1991 | Yelderman et al. | 128/511 |
| 5,111,827 | 5/1992 | Rantala | 128/719 |
| 5,140,993 | 8/1992 | Opekun, Jr. et al. | 128/730 |
| 5,171,535 | 12/1992 | Lamont | 422/85 |
| 5,178,155 | 1/1993 | Mault | 128/718 |
| 5,193,551 | 3/1993 | Pilipski | 128/716 |
| 5,291,898 | 3/1994 | Wolf | 128/719 |
| 5,293,875 | 3/1994 | Stone | 128/718 |
| 5,303,712 | 4/1994 | Van Duren | 128/716 |
| 5,328,664 | 7/1994 | Ponsy | 422/84 |
| 5,361,771 | 11/1994 | Craine et al. | 128/719 |
| 5,383,469 | 1/1995 | Vreman et al. | 128/719 |

OTHER PUBLICATIONS

Howard et al., Computerized Cardiopulmonary Stress Testing in Children, IEEE, pp. 648–661 1979.

*Primary Examiner*—Jennifer Bahr
*Assistant Examiner*—Stephen Huane
*Attorney, Agent, or Firm*—Webb Ziesenheim Bruening Logsdon Orkin & Hanson, P.C.

[57] ABSTRACT

A breath gas analysis module for supplying a sample gas to a gas detector includes a manifold having a body defining a chamber therein. The chamber includes a main passage extending through the manifold body, an outlet passage extending into the manifold body from an outlet end at a base of the manifold body and toward the main passage and a metering orifice extending between and in fluid communication with the main passage and an interior end of the outlet passage. An inlet tube is attached to the manifold body at one end of the main passage and defines an internal passage in fluid communication with the main passage. A collection tube is attached to the manifold body at another end of the main passage and defines an internal passage in fluid communication with the main passage. A check valve is positioned within the inlet tube internal passage and is oriented to permit fluid flow into, but not back from, the main passage. A resilient gas reservoir is attached to a free end of the collection tube opposite an end thereof attached to the manifold body. The resilient gas reservoir defines a storage chamber therein which is in fluid communication with the collection tube internal passage.

23 Claims, 10 Drawing Sheets

BREATH GAS ANALYSIS MODULE

BACKGROUND OF THE INVENTION

1. Field of the Invention

This invention relates to the detection of gases and, more particularly, to a device for providing a gas sample to a gas detector, such as a portable gas detector.

2. Description of the Prior Art

Carbon monoxide is a highly toxic, non-irritating, odorless, colorless gas. In a typical home, furnaces, gas stoves, space heaters, fire places and even automotive exhaust are all potential sources for carbon monoxide. Because carbon monoxide is absorbed into the bloodstream two hundred times more easily than oxygen, and remains in the blood for hours after exposure, even relatively low levels of carbon monoxide exposure can, over time, result in sickness, headaches, nausea or death. Although deaths from carbon monoxide poisoning have dropped in recent years, there still continues to be a large number of deaths per year which can be attributed to carbon monoxide from fuel-burning appliances which are operating inefficiently or which are improperly vented.

Figure 1:
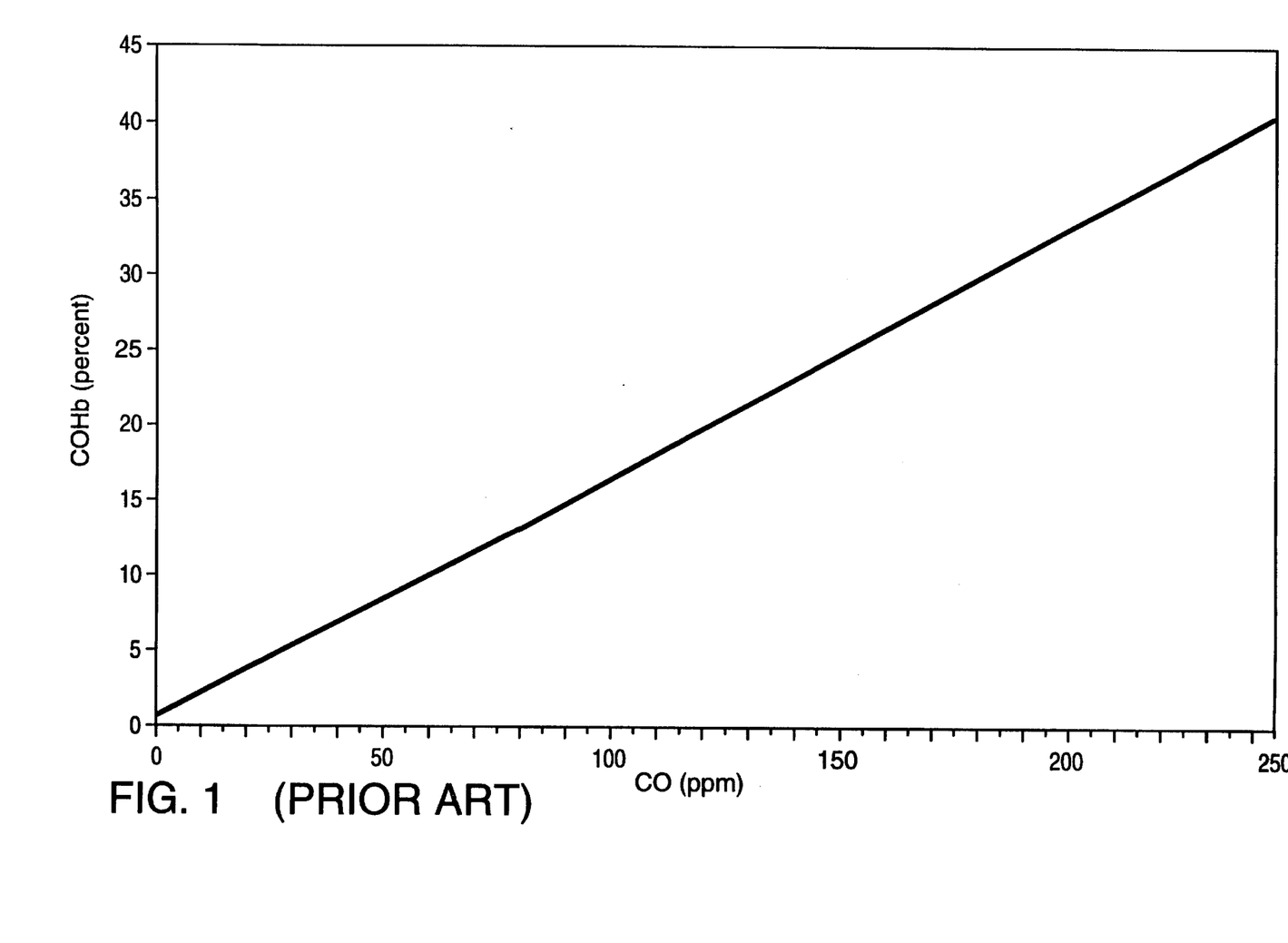
FIG. 1 is a graph showing the relationship of expired carbon monoxide to carboxyhemoglobin level in the blood.

The public is more aware today of the danger of carbon monoxide than in the past. Home detectors of carbon monoxide are now readily available on the market and are being used in much the same manner as home fire and smoke detectors. When a carbon monoxide alarm incident is responded to, the professionals involved, who can include EMT personnel, utility personnel or service technicians, usually recommend that the residents leave the house and then air out the house. After the house has been aired out, the appropriate professional personnel can return to the house to locate and repair the source of the unwanted carbon monoxide. Although persons exposed to carbon monoxide can be tested for the level of exposure through a blood test, such an invasive test must be carried out in a hospital or other facility which has access to a complicated blood analysis machine. Since carbon monoxide is a cumulative poison with a half-life of about four to five hours, an analysis to determine the level of carboxyhemoglobin (COHb) in the bloodstream can serve as a verification of a true carbon monoxide exposure, help to determine if medical attention is needed and determine the level of medical attention which is appropriate. Analysis of COHb in the blood is a time-consuming process which, as discussed above, involves use of a special machine and a sample of the person's blood. Medical studies have shown that the concentration of carbon monoxide gas in the alveoli (air sacks of the lungs) has a linear and consistent relationship to the COHb measured in the blood. This relationship is shown in FIG. 1 of the accompanying drawings. The COHb reading based on a person's breath sample can be used as an indicator of approximate COHb levels, but it is not a substitute for a blood test to determine exact COHb levels.

It is, accordingly, an object of the present invention to provide a device for readily and easily measuring, at least to a first order level, the levels of COHb in a person's bloodstream by analyzing a sample of the person's breath for the levels of carbon monoxide present therein. This measurement can be used to verify whether a person has been exposed to carbon monoxide and the severity of the exposure, and to determine the nature or level of the medical care necessary for such exposure. It is also an object of the present invention to provide such a measurement device which can be used in connection with a portable gas detector and which also can be used to measure various other gases or other substances from a person's breath sample.

SUMMARY OF THE INVENTION

Accordingly, we have invented a breath gas analysis module for supplying a sample gas to a gas detector. The module includes a manifold having a body defining a chamber therein. The chamber includes a main passage extending through the manifold body, an outlet passage extending into the manifold body from an outlet end at a base of the manifold body and toward the main passage and a metering orifice extending between and in fluid communication with the main passage and an interior end of the outlet passage. An inlet tube is attached to the manifold body at one end of the main passage and defines an internal passage in fluid communication with the main passage. A collection tube is attached to the manifold body at another end of the main passage and also defines an internal passage in fluid communication with the main passage. A check valve is positioned within the inlet tube internal passage and is oriented to permit fluid flow into, but not back from, the main passage. A resilient gas reservoir is attached to a free end of the collection tube opposite an end thereof attached to the manifold body. The resilient gas reservoir defines a storage chamber therein which is in fluid communication with the collection tube internal passage.

The breath gas analysis module of the present invention can also include a tubular mouthpiece, such as a disposable cardboard tube, positioned over a free end of the inlet tube opposite an end thereof attached to the manifold body. The mouthpiece defines an internal passage which contacts an outer surface of the inlet tube and which is in fluid communication with the inlet tube internal passage.

The resilient reservoir can be a balloon. The collection tube can include a groove extending around its external surface near its free end and an open end of the balloon is attached to the external surface of the collection tube by the groove. A filter disc can be positioned within and cover the inlet tube internal passage adjacent a free end of the inlet tube opposite the end thereof attached to the manifold body. The manifold body can include a groove within the outlet passage located near the outlet end and a resilient O-ring which is retained by this groove and extends into the outlet passage.

The breath gas analysis module of the present invention can also include an exhaust pin hole extending through the manifold body, separate from the manifold chamber. The exhaust pin hole terminates at the base of the manifold body and an exhaust pin is positioned within the exhaust pin hole. The exhaust pin can include a handle at an upper end thereof opposite a lower end at the base of the manifold body. The module can also include means for biasing the lower end of the exhaust pin out of the manifold body, such as a retaining ring and spring arrangement. A cap can be positioned on the lower end of the exhaust pin.

The features of the module described above can be provided as a separate device, can be attached to an existing gas detector, such as a portable gas detector, or can be built into a gas detector to form a dedicated product.

DESCRIPTION OF THE PREFERRED EMBODIMENTS

A preferred embodiment of a breath gas analysis module 10 of the present invention is shown in FIGS. 2–11. The module 10 includes a manifold 12 having a body 14 which defines a manifold chamber 16 therein. The manifold body 14 is shown in the drawings as a rectangular block having a top 18, bottom or base 20, front 22, rear 24 and sides 26 and 28. Other configurations for the manifold body 14 could be used and remain within the scope and intentions of the present invention. The manifold chamber 16 in the manifold 12 includes a main passage 30 extending through the manifold body 14 from side 26 to side 28. The main passage 30 at side 26 opens into a wider inlet end 32 and, similarly, the main passage 30 at side 28 opens into a wider collection end 34. The manifold chamber 16 also includes an outlet passage 36 which extends into the manifold body 14 toward the main passage 30 from an outlet end 38 at the base 20 to an interior end 40 adjacent the main passage 30. The manifold chamber 16 also includes a metering or regulating orifice 42 which extends from the interior end 40 of the outlet passage 36 to the main passage 30 and provides fluid communication therebetween.

The module 10 includes an inlet tube 44 which is attached to the manifold body 14 at the inlet end 32 of the main passage 30 and includes an inlet tube internal passage 46 therethrough and in fluid communication with the main passage 30. An end 48 of the inlet tube 44 adjacent the manifold body 30 has a reduced outer diameter so that it fits in the inlet end 32 of the main passage 30. Similarly, the module 10 includes a collection tube 50 which is attached to the manifold body 14 at the collection end 34 of the main passage 30 and includes a collection tube internal passage 52 which is in fluid communication with the main passage 30. An end 54 of the collection tube 50 adjacent the manifold body 30 has a reduced other diameter so that it fits securely within the collection end 34 of the main passage 30. The manifold body 14, inlet tube 44 and collection tube 50 are ideally made of PVC or other plastic materials and are secured together with an appropriate adhesive.

Figure 2:
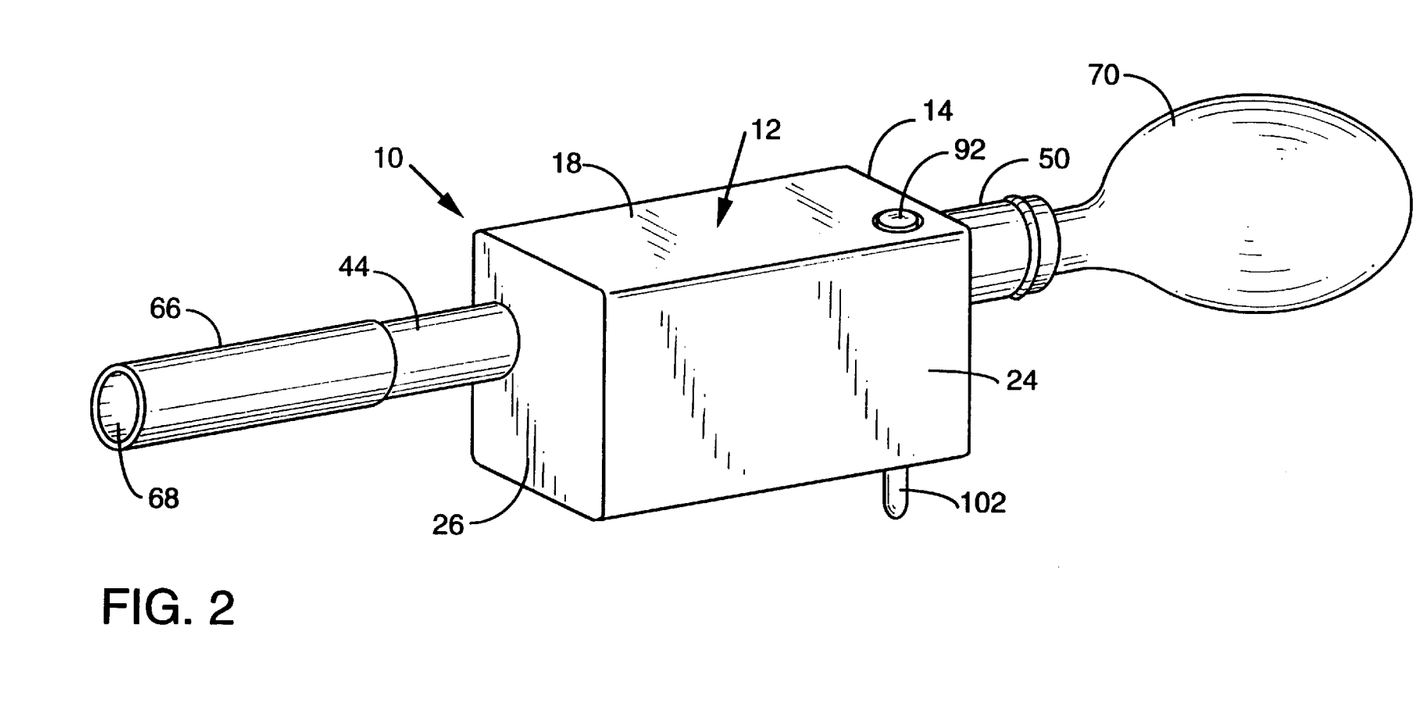
FIG. 2 is a rear perspective view of a breath gas analysis module in accordance with the present invention.
Figure 3:
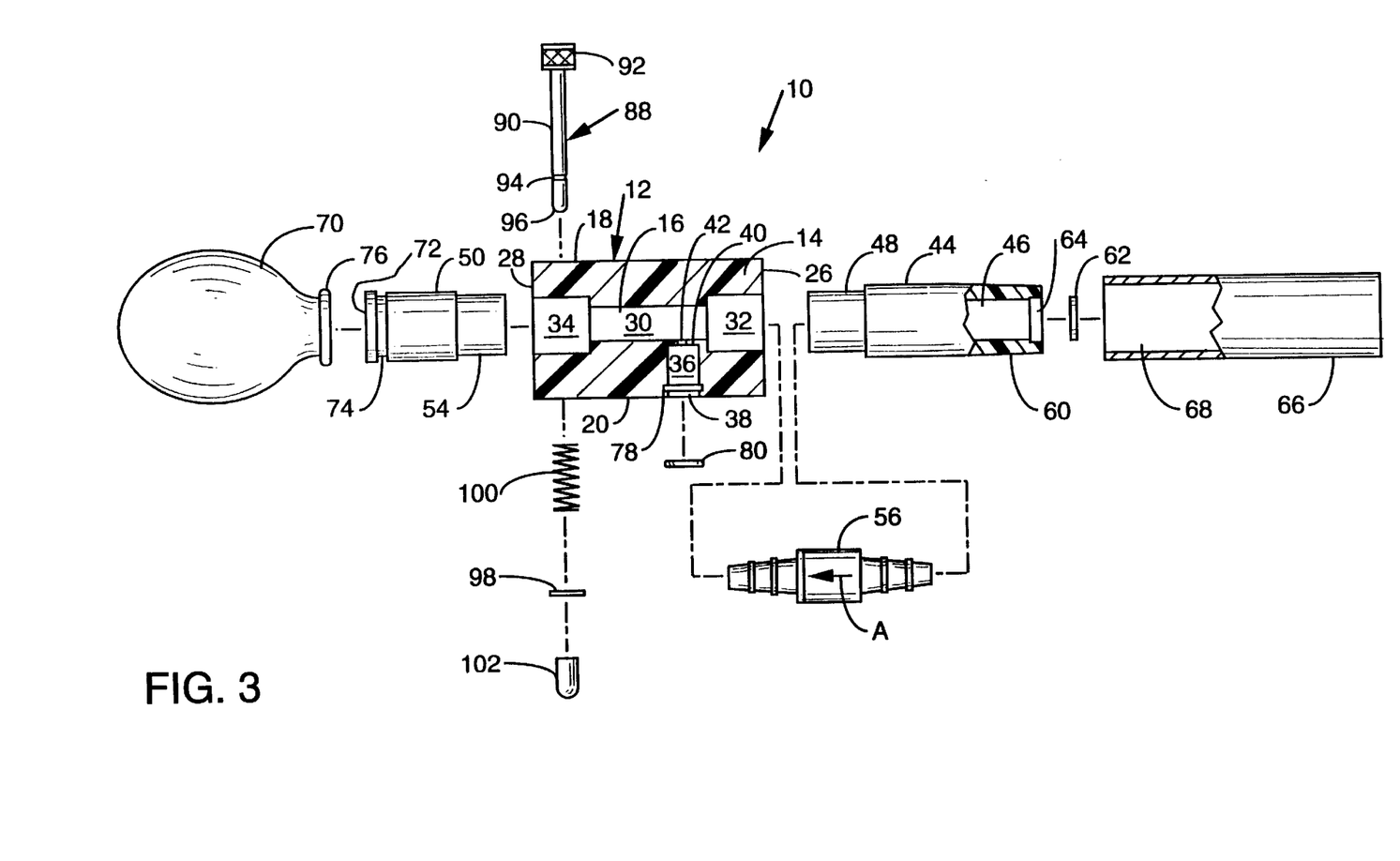
FIG. 3 is an exploded, front elevational view of the breath gas analysis module shown in FIG. 2.
Figure 9:
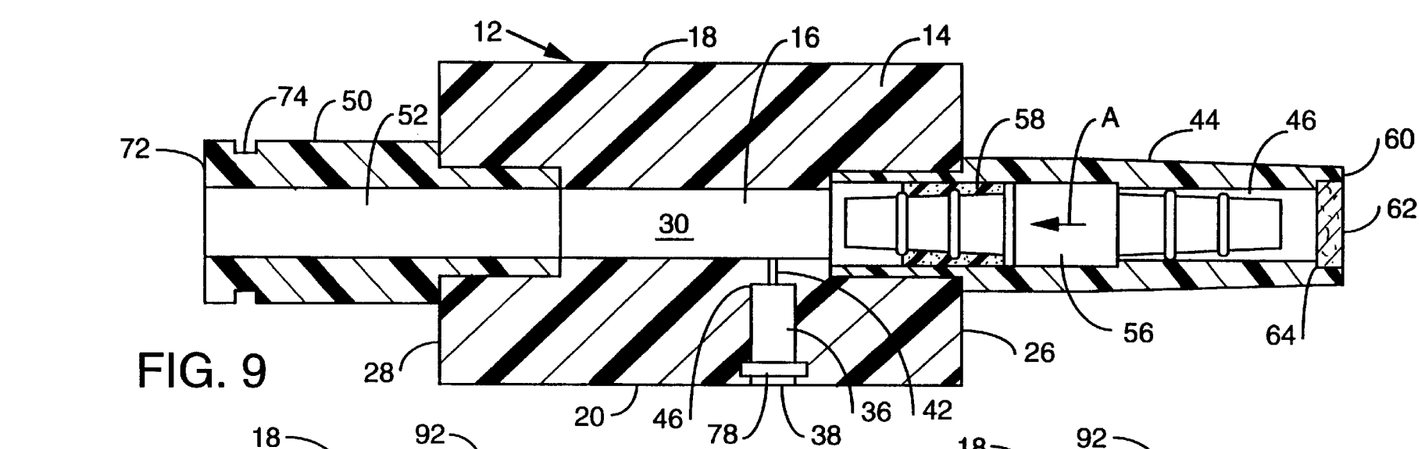
FIG. 9 is a section taken along lines IX—IX in FIG. 6, with the O-ring removed.
Figure 10:
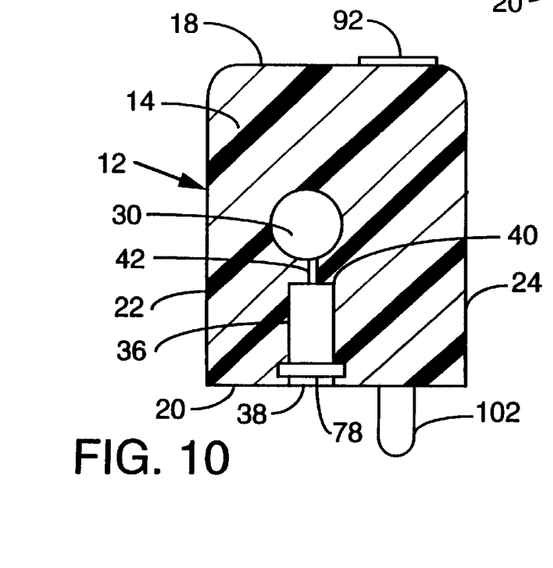
FIG. 10 is a section taken along lines X—X in FIG. 6, with the O-ring removed.
Figure 11:
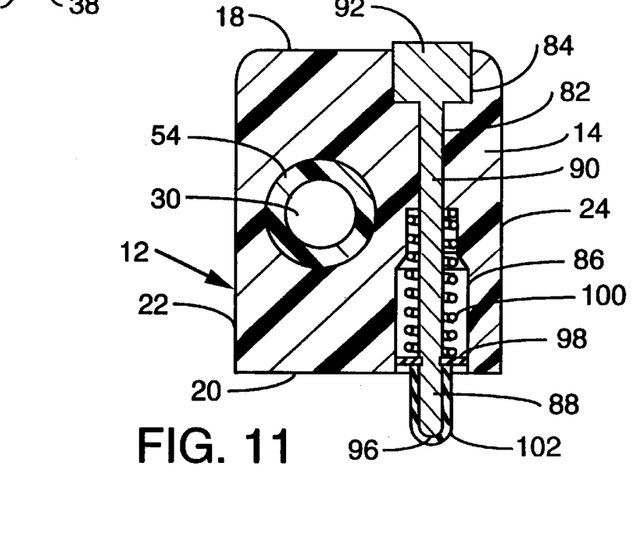
FIG. 11 is a section taken along lines XI—XI in FIG. 5.
Figure 12:
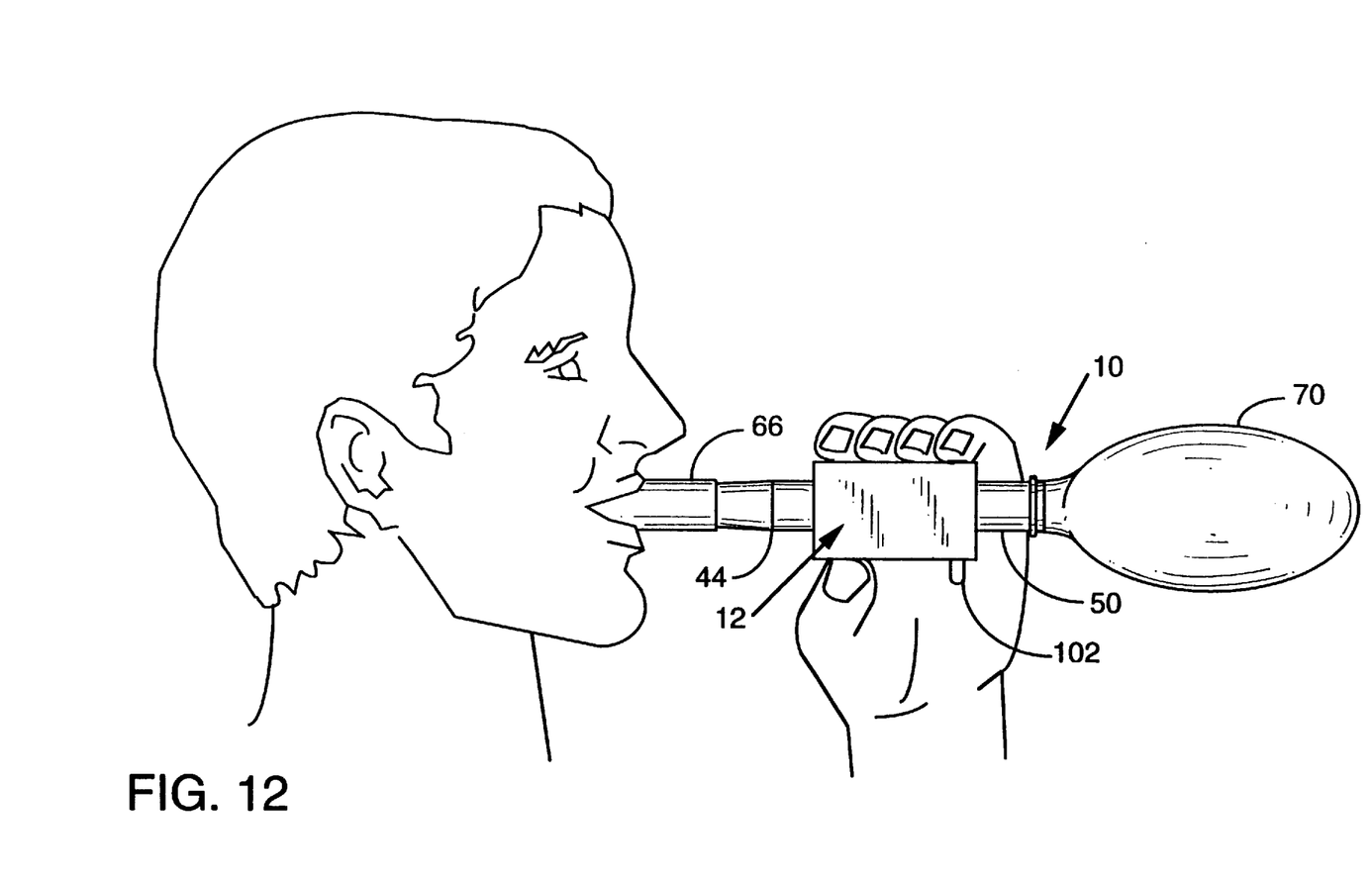
FIG. 12 is a rear elevational view of the breath gas analysis module of FIG. 2 showing the storage balloon being inflated.
Figure 13:
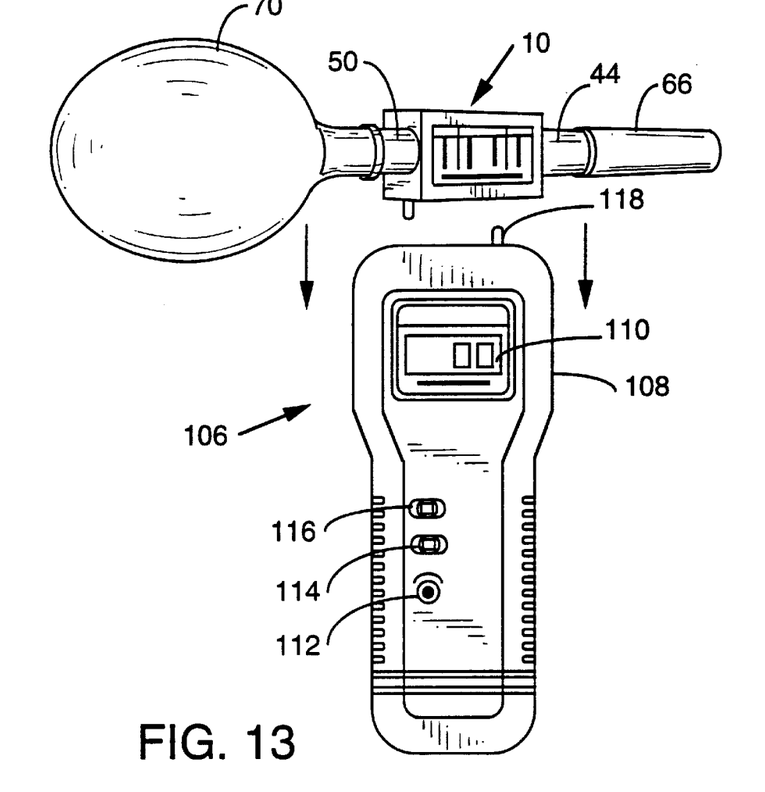
FIGS. 13–16 are a series of views showing the breath gas analysis module of FIG. 2, after the storage balloon has been inflated as shown in FIG. 12, being installed onto a portable gas detector.
Figure 14:
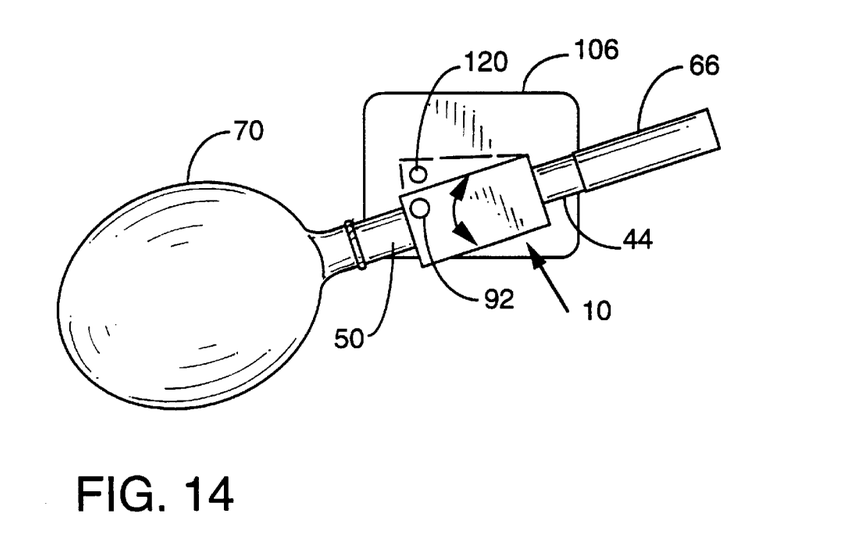
Figure 15:
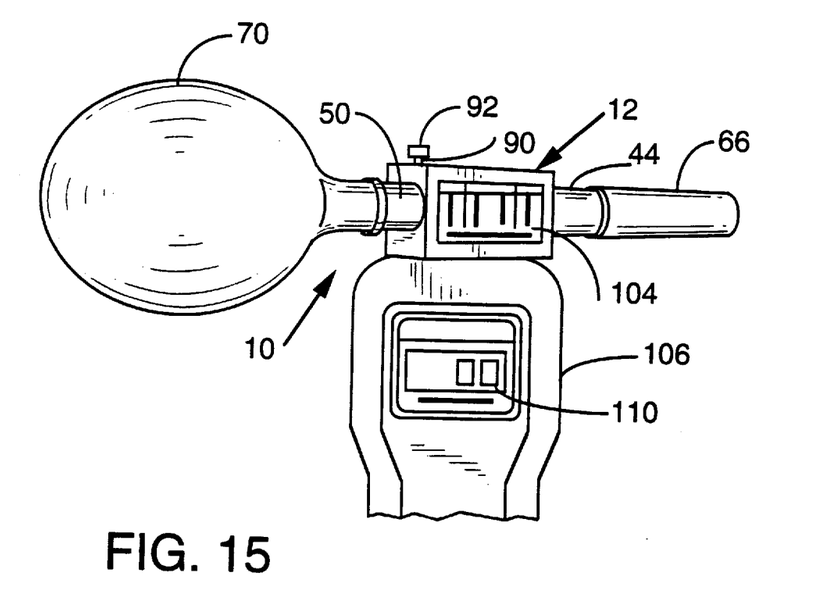
Figure 16:
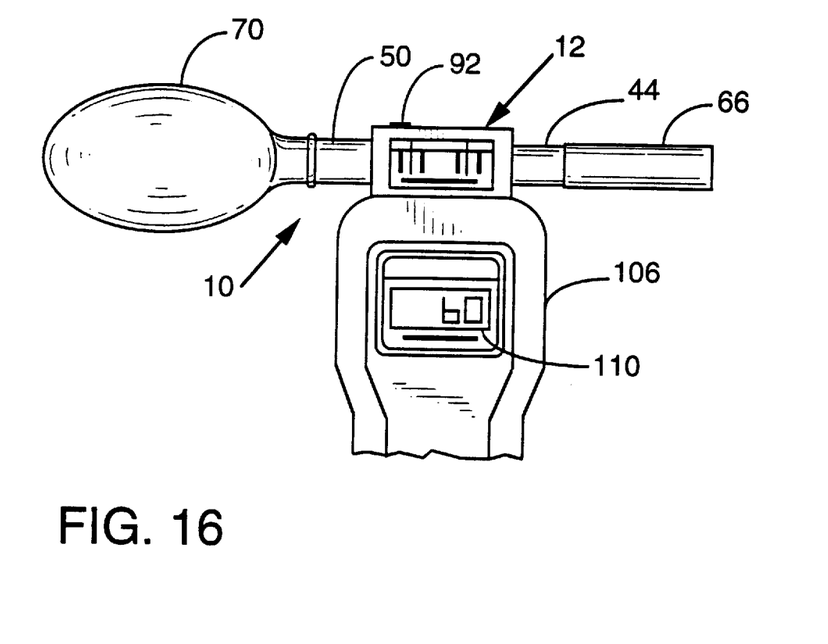

A check valve 56 is positioned within the inlet tube 44 in its internal passage 46 and controls all fluid flow therethrough. In accordance with the present invention, the check valve 56 is oriented in the direction of the arrow A shown in FIGS. 3 and 9 so that fluid flow is permitted into the main passage 30, but back flow is not permitted out of the main passage 30. The importance of this one-way check valve 56 in the present invention will be discussed hereinafter in more detail. The check valve 56 can be securely fastened to the inlet tube 44 by a quantity of adhesive 58, such as epoxy or the like, as shown in FIG. 9. A free end 60 of the inlet tube 44 opposite end 48 can include a filter disc 62 positioned therein and secured thereto by being press fit within a flared area 64 the internal passage 46 of the inlet tube 44 adjacent free end 60. As shown in FIGS. 2 and 3, a tubular mouthpiece 66, having its own internal passage 68 therethrough, is positioned over the free end 60 of the inlet tube 44 and extends outwardly therebeyond. The internal passage 68 of the mouthpiece 66 contacts an outer surface of the inlet tube 44 near its free end 60 to frictionally attach the mouthpiece 66 to the inlet tube 44. The internal passage 68 of the mouthpiece 66 is in fluid communication with the internal passage 46 of the inlet tube 44. The mouthpiece 66 is readily removable from the inlet tube 44 and is preferably made of cardboard so that it is disposable.

A resilient gas reservoir, such as a balloon 70 shown in FIGS. 2 and 3, is attached to a free end 72 of the collection tube 50 opposite end 54. The balloon 70 defines a storage chamber therein which is in fluid communication with the internal passage 52 of the collection tube 50. Preferably, the collection tube 50 includes a groove 74 extending around its external surface at free end 72 and is configured to receive a thick ring 76 provided around the open end of the balloon 70. In this manner, the balloon 70 is readily attachable to the collection tube 50 and held in place by groove 74. In addition, groove 74 permits the balloon 70 to be removed from the collection tube 50 and replaced as needed.

The breath gas analysis module 10 of the present invention can also include a groove 78 in the manifold body 14 within the outlet passage 36 and located near its outlet end 38. A resilient O-ring 80 or the like can be positioned within groove 78 and extend into the outlet passage 36. The purpose and function of O-ring 80 will be discussed hereinafter in more detail.

The breath gas analysis module 10 of the present invention can also include an exhaust pin hole 82 which extends through the manifold body 14 from the top 18 to the bottom 20. The upper end 84 and lower end 86 of the exhaust pin hole are, as shown in more detail in FIG. 11, wider than the remaining portion thereof. An exhaust pin 88 is positioned within and extends through the exhaust pin hole 82. The exhaust pin 88 has an elongated shank 90 attached to a wider handle 92 at an upper end thereof. The shank 90 of the exhaust pin 88 is slightly narrower than and slides within the area of the exhaust pin hole 82 between upper end 84 and lower end 86. The handle 92 is configured to fit within the upper end 84 of the exhaust pin hole 82. A groove 94 is provided near the lower end 96 of the exhaust pin 88 on its outer surface and is configured to receive a retaining ring 98 therein. A spring 100 is positioned within the lower end 86 of the exhaust pin hole 82 and surrounds the shank 90 of the exhaust pin 88. The spring 100 extends from and contacts the retaining ring 98 and extends upwardly into and contacts the manifold body 14 where the lower end 86 of the exhaust pin hole 82 terminates. In this manner, the spring 100 provides a resilient means for biasing the lower end 96 of the exhaust pin 88 out of the manifold body 14. It is preferred that the exhaust pin 88 be made of a metal material and that the lower end 96 of the exhaust pin 88 be covered with an end cap 102 made of rubber or the like. In addition, it is preferred that the handle 92 of the exhaust pin 88 be colored bright red or the like and be normally positioned within the upper end 84 of the exhaust pin hole 82 and not extend above, or much above, the top 18 of the manifold body 14.

Figure 4:
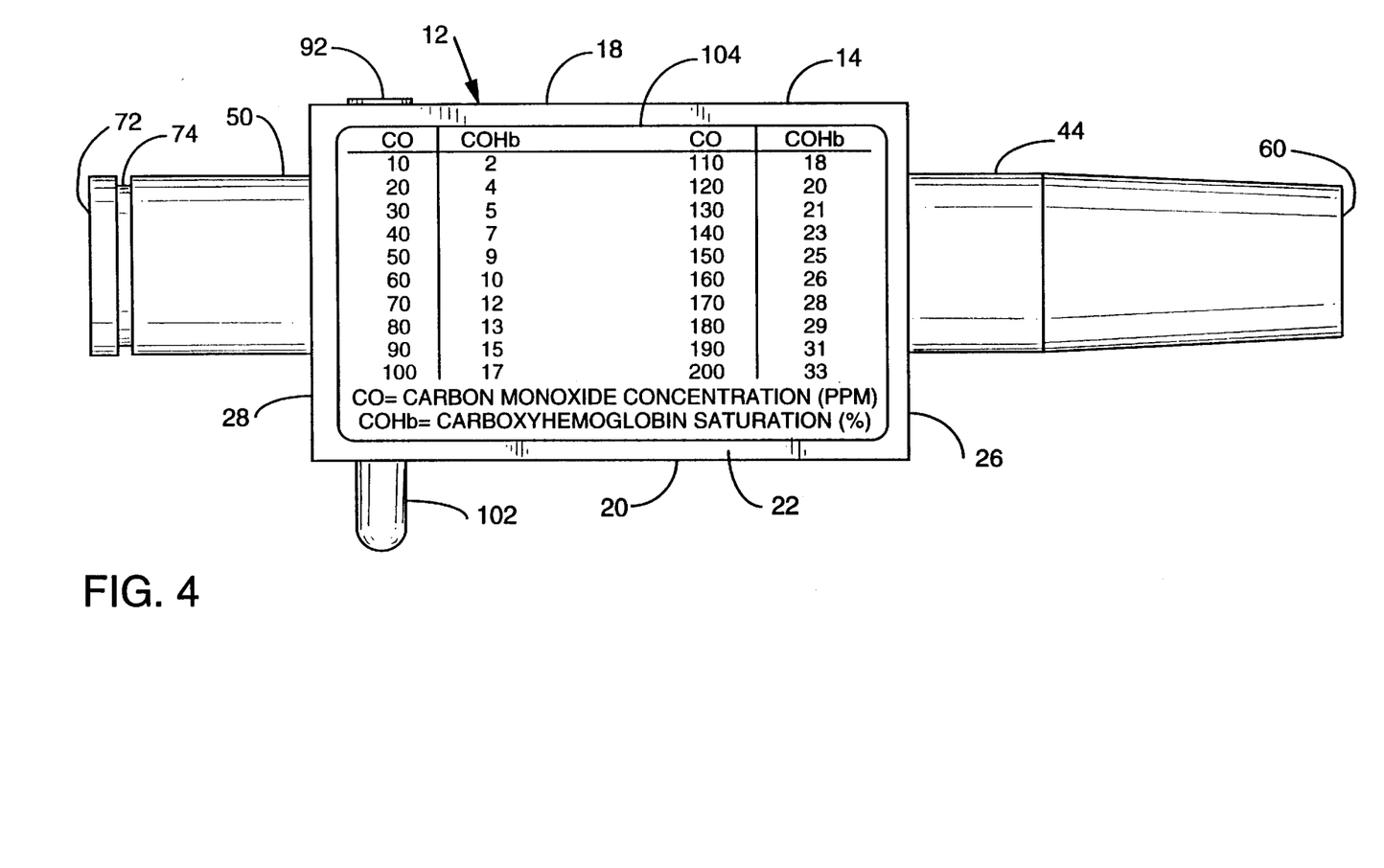
FIG. 4 is a front view of the breath gas analysis module shown in FIG. 2, with the balloon and mouthpiece removed.
Figure 5:
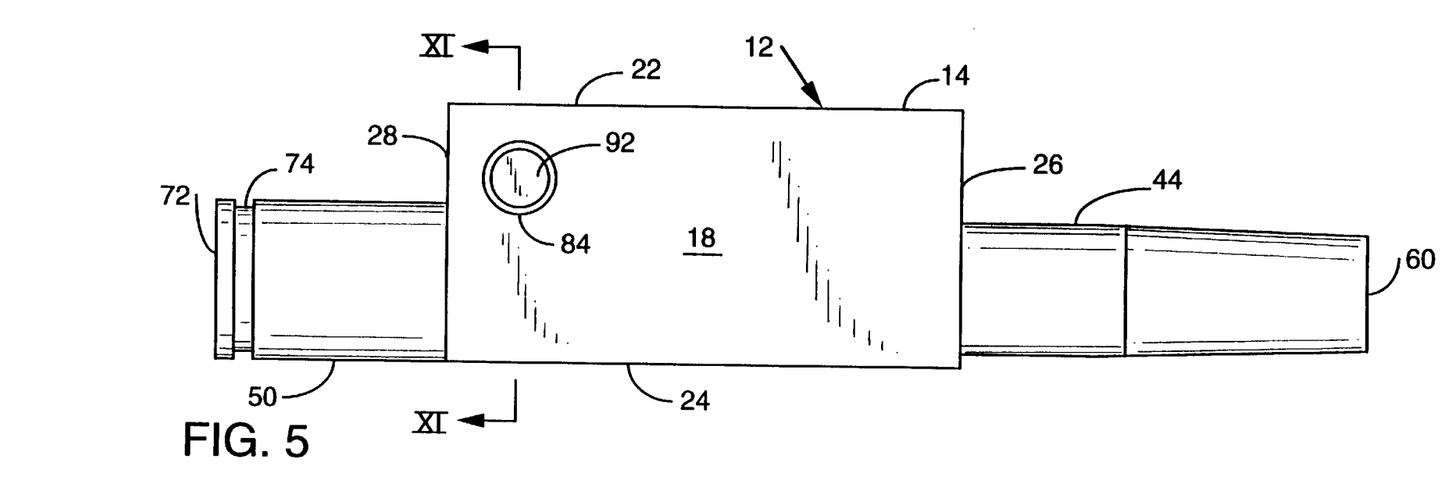
FIG. 5 is a top plan view of the breath gas analysis module shown in FIG. 4.
Figure 6:
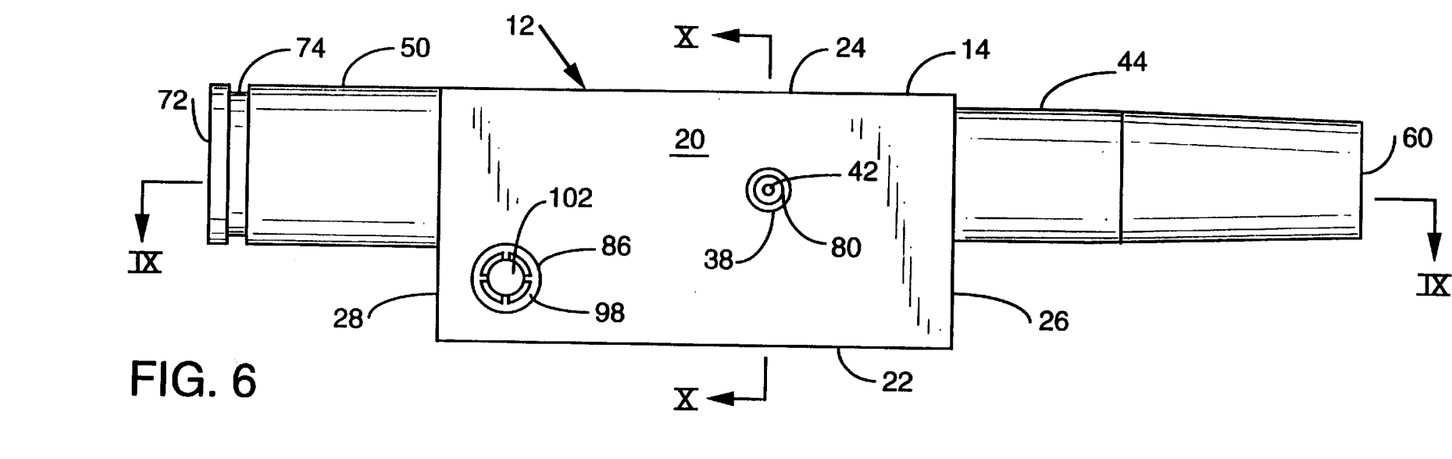
FIG. 6 is a bottom plan view of the breath gas analysis module shown in FIG. 4.
Figure 7:
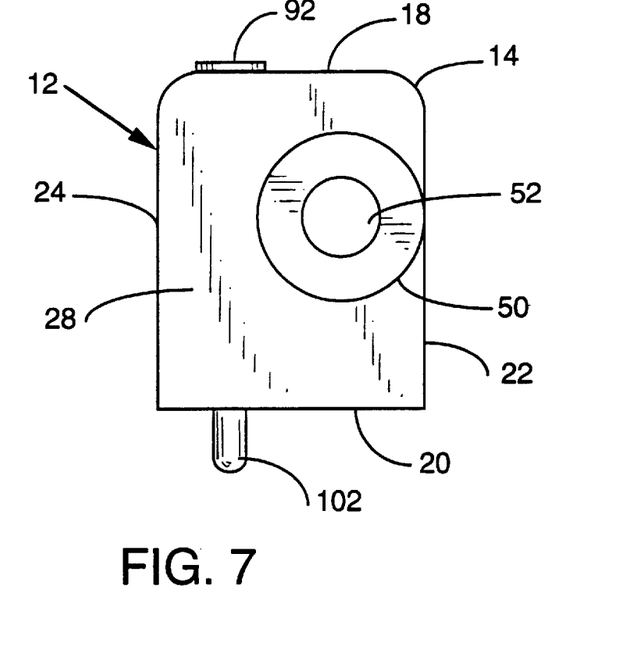
FIG. 7 is a view from one side of the breath gas analysis module shown in FIG. 4.
Figure 8:
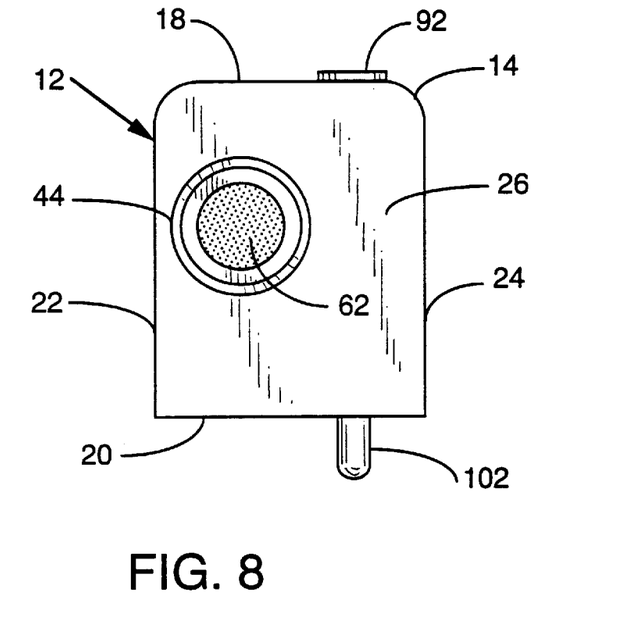
FIG. 8 is a view from the other side of the breath gas analysis module shown in FIG. 4.

As shown in FIG. 4, the front 22 of the breath gas analysis module can include a label 104 with a chart which correlates the measured carbon monoxide level in a breath sample to the carboxyhemoglobin level in the bloodstream of the person providing the breath sample. This label 104 is based on the information in the graph shown in FIG. 1.

FIGS. 12–16 show how the breath gas analysis module 10 of the present invention, as shown in FIGS. 2–11 above, can be used to measure a gas, such as carbon monoxide, or other substance in a breath sample. Initially, a person grasps the manifold body 14 of the module 10 and places a thumb over the outlet end 38 of the outlet passage 36. The person then blows one or more times into the mouthpiece 66. The breath blown therein travels through the internal passage 68 of the mouthpiece 66, through the check valve 56 in the inlet tube 44, through the main passage 30, through the internal passage 52 of the collection tube 50 and into the balloon 70. Since it is advisable to obtain as large of a quantity of a breath sample as possible, it is preferred that the balloon 70 be filled to a reasonably large degree by the person having the breath sample taken. Stretching the balloon 70 as much as possible also aids to force the breath sample back out of the balloon 70 for analysis. While this may be done by some persons with one breath, it is expected that four or five breaths will be needed to sufficiently fill the balloon 70. Through the use of the check valve 56 in the inlet tube 44, a person can take one breath and blow into the breath gas analysis module 10 of the present invention and then remove his or her mouth from the mouthpiece 66 in preparation for a subsequent breath. With the outlet end 38 of the outlet passage 36 securely closed by the person's thumb or the like, no breath sample will escape from the balloon 70 through the inlet tube 44.

After the balloon 70 has been sufficiently filled, the breath gas analysis module 10 is positioned on top of a portable gas detector or the like. The gas detector 106 shown in FIGS. 13–16 is representative of the prior art gas detectors. More detailed information about this particular gas detector is shown in U.S. Pat. No. 5,018,395, the disclosure of which is incorporated herein by reference. Gas detector 106 includes a housing 108 enclosing the working elements of the gas detector 106, including a gas sensor particularly designed for measuring the gas or other substance of interest in the breath sample. The gas detector 106 also includes a display 110, a zero set button 112, a power button 114 and a light button 116 on the front of the device. In addition, the gas detector 106 includes an inlet nipple 118 or other inlet port as well as an exhaust port 120, shown as a recessed hole rather than as an exhaust nipple as shown in U.S. Pat. No. 5,1018,395.

The breath gas analysis module 10, with the balloon 70 filled as discussed above, is brought close to the gas detector 106 with the outlet passage 36 still manually closed off. The thumb is removed from the outlet end 38 of the outlet passage 36 and the module 10 is positioned with its base 20 above the top of the gas detector 106. The module 10 is then brought into contact with the gas detector 106, with the inlet nipple 118 positioned within the outlet passage 36. The O-ring 80 within the outlet passage 36 at its outlet end 38 provides a tight fit between the module 10 and the gas detector 106.

When the module 10 is brought into contact with the gas detector 106, it is preferred that the module 10 be oriented at a slight angle thereto so that the exhaust port 120 of the gas detector 106 is not covered. This action will force the exhaust pin 88 up into the exhaust pin hole 82, compressing spring 100 therein and moving handle 92 of the exhaust pin 88 out of the exhaust pin hole 82 and well above the top 18 of the manifold body 14. This is shown in more detail in FIGS. 14 and 15. Module 10 can then be rotated more completely on top of the gas detector 106 until the exhaust pin 88 becomes aligned with the exhaust port 120. At that point, exhaust pin 88, through the action of the spring 100, will be forced securely down into exhaust port 120 of the gas detector 106. A clear visual indication of the mating of the exhaust pin 88 with the exhaust port 120 is provided when the handle 92 of the exhaust pin 88 once again retracts into the manifold body 14. This is shown more clearly in connection with FIG. 16.

At this point, the balloon 70, due to its resilient material and its prior elongation due to inflation, releases the gas sample therein back through the internal passage 52 of the collection tube 50, into the main passage 30 and then through the orifice 42 and outlet passage 36 and into the inlet nipple 118 of the gas detector 106. The orifice 42 is significantly smaller than the main passage 30 and outlet passage 36 and is sized accordingly to control the flow rate of the gas sample to the sensor within the gas detector 106. In this manner, and in conjunction with the substantial blocking of the exhaust port 120 of the gas detector 106, a sufficient gas sample will be passed for a sufficiently long period of time across the sensor of the gas detector 106 to obtain a satisfactory and accurate reading. Once a reading has been made of the carbon monoxide level in the gas sample, as indicated by the display 110, an appropriate correlation can be made to the carboxyhemoglobin level in the person's blood through the use of label 104 shown in FIG. 4.

Although the breath gas analysis module 10 of the present invention has been shown in the drawings and described above as a separate module which is adapted to be attached to an existing gas detector, it is to be understood that such a module 10 can be incorporated permanently into a structure for a dedicated gas detector. In addition, the module 10 can be readily configured to work with a variety of existing gas detectors, such as by appropriately sizing and locating the outlet passage 36 and exhaust pin 88, by eliminating the exhaust pin 88, or by otherwise configuring the module 10 to meet the particular physical requirements of a particular gas detector.

It can be seen that the present invention provides a non-invasive method of testing for carbon monoxide or other substances dissolved in a person's bloodstream. It is a portable device which is field useable and is easy to use. The device provides the opportunity to check persons exposed to carbon monoxide or other materials without the use of a time-consuming, expensive and invasive blood test. The inventors expect that the principal use of the present invention will be for emergency personnel to determine whether a person has been seriously exposed to carbon monoxide poisoning and needs further treatment. In addition, the device can also be used to determine whether workers potentially exposed to carbon monoxide in the workplace have actually been so exposed or whether such workers are using required masks, respirators or the like on the job. In addition, the device can be used to determine whether a person is a nonsmoker or has kept a promise to stop smoking. Medical offices can also use this device for routine screening of patients, particularly in the winter season, to see if they have been exposed to high carbon monoxide levels.

In this manner, medical personnel can determine whether a patient's flu-like symptoms may have been caused by exposure to carbon monoxide.

Having described presently preferred embodiments of the present invention, it is to be understood that the invention may be otherwise embodied within the scope of the appended claims.

We claim:

1. A breath gas analysis module for supplying a sample gas to a gas detector, said module comprising:
   a) a manifold having a body defining a chamber therein, the chamber including a main passage extending through the manifold body, an outlet passage extending into the manifold body from an outlet end at a base of the manifold body and toward said main passage, and a metering orifice extending between and in fluid communication with the main passage and an interior end of the outlet passage;
   b) an inlet tube attached to the manifold body at one end of the main passage and defining an internal passage in fluid communication with the main passage;
   c) a collection tube attached to the manifold body at another end of the main passage and defining an internal passage in fluid communication with the main passage; tube internal passage and oriented to permit fluid flow into, but
   d) a resilient gas reservoir attached to a free end of the collection tube opposite an end thereof attached to the manifold body, the resilient gas reservoir defining a storage chamber therein which is in fluid communication with the collection tube internal passage; and
   e) a check valve in said module between the metering orifice and a free end of the inlet tube opposite the main passage body and oriented to permit fluid flow into, but no back flow from, the main passage and the resilient gas reservoir when the outlet end of the outlet passage is closed.

2. The breath gas analysis module of claim 1 further including a tubular mouthpiece positioned over a free end of the inlet tube opposite an end thereof attached to the manifold body, the mouthpiece defining an internal passage which contacts an outer surface of the inlet tube and which is in fluid communication with the inlet tube internal passage.

3. The breath gas analysis module of claim 2 wherein the mouthpiece is made of cardboard.

4. The breath gas analysis module of claim 1 wherein the resilient reservoir is a balloon.

5. The breath gas analysis module of claim 4 wherein the collection tube includes a groove extending around its external surface near the free end thereof and an open end of the balloon is attached to the external surface of the collection tube by said groove.

6. The breath gas analysis module of claim 1 further including a filter disc positioned within and covering the inlet tube internal passage and adjacent a free end of the inlet tube opposite an end thereof attached to the, manifold body.

7. The breath gas analysis module of claim 1 further including a groove in the manifold body within the outlet passage and located near the outlet end, and a resilient O-ring retained by said groove and extending into the outlet passage.

8. The breath gas analysis module of claim 1 wherein the manifold body further defines an exhaust pin hole extending therethrough and separate from the manifold chamber, the exhaust pin hole terminating at the base of the manifold body, and the breath gas analysis module further including an exhaust pin positioned within the exhaust pin hole and including a handle at an upper end thereof opposite a lower end at the base of the manifold body, and means for biasing the lower end of the exhaust pin out of the manifold body.

9. The breath gas analysis module of claim 8 wherein the exhaust pin hole includes a wider area adjacent the base of the manifold body, wherein the exhaust pin includes a groove on an outer surface thereof near its lower end, and wherein the biasing means includes a retaining ring attached to the exhaust pin groove and a spring surrounding the exhaust pin above and contacting the retaining ring and positioned within the wider area of the exhaust pin hole.

10. The breath gas analysis module of claim 9 further including a cap positioned on the lower end of the exhaust pin.

11. The breath gas analysis module of claim 1 wherein the check valve is positioned within the inlet tube internal passage.

12. An apparatus for analyzing a breath gas for a sample gas, said apparatus comprising:
   a) a gas detector having an inlet port;
   b) a manifold having a body defining a chamber therein, the chamber including a main passage extending through the manifold body, an outlet passage in fluid communication with the gas detector inlet port and extending into the manifold body from a base thereof and toward said main passage, and a metering orifice extending between and in fluid communication with the main passage and an interior end of the outlet passage;
   c) an inlet tube attached to the manifold body at one end of the main passage and defining an internal passage in fluid communication with the main passage;
   d) a collection tube attached to the manifold body at another end of the main passage and defining an internal passage in fluid communication with the main passage;
   e) a resilient gas reservoir attached to a free end of the collection tube opposite an end thereof attached to the manifold body, with the resilient gas reservoir defining a storage chamber therein which is in fluid communication with the collection tube internal passage; and
   f) a check valve in said module between the metering orifice and a free end of the inlet tube opposite the main passage body and oriented to permit fluid flow into, but no back flow from, the main passage and the resilient gas reservoir.

13. The apparatus of claim 12 further including a tubular mouthpiece positioned over a free end of the inlet tube opposite an end thereof attached to the manifold body, the mouthpiece defining an internal passage which contacts an outer surface of the inlet tube and which is in fluid communication with the inlet tube internal passage.

14. The apparatus of claim 12 wherein the mouthpiece is made of cardboard.

15. The apparatus of claim 12 wherein the resilient reservoir is a balloon.

16. The apparatus of claim 15 wherein the collection tube includes a groove extending around its external surface near the free end thereof and an open end of the balloon is attached to the external surface of the collection tube by said groove.

17. The apparatus of claim 12 further including a filter disc positioned within and covering the inlet tube internal passage and adjacent a free end of the inlet tube opposite an end thereof attached to the manifold body.

18. The apparatus of claim 12 wherein the manifold body further defines an exhaust pin hole extending therethrough and separate from the manifold chamber, the exhaust pin hole terminating at the base of the manifold body, and the breath gas analysis module further including an exhaust pin positioned within the exhaust pin hole and including a handle at an upper end thereof opposite a lower end at the base of the manifold body, and means for biasing the lower end of the exhaust pin out of the manifold body and in contact with an exhaust port in said gas detector.

19. The apparatus of claim 18 wherein the exhaust pin hole includes a wider area adjacent the base of the manifold body, wherein the exhaust pin includes a groove on an outer surface thereof near its lower end, and wherein the biasing means includes a retaining ring attached to the exhaust pin groove and a spring surrounding the exhaust pin above and contacting the retaining ring and positioned within the wider area of the exhaust pin hole.

20. The breath gas analysis module of claim 12 wherein the check valve is positioned within the inlet tube internal passage.

21. A breath gas analysis module for supplying a sample gas to a gas detector, said module comprising:
 a) a manifold having a body defining a chamber therein, the chamber including a main passage in the manifold body, an outlet passage extending into the manifold body and toward said main passage, and a metering orifice extending between and in fluid communication with the main passage and an interior end of the outlet passage;
 b) an inlet passage in the manifold body in fluid communication with the main passage;
 c) a collection passage in the manifold body and in fluid communication with the main passage;
 d) a check valve in the inlet passage and oriented to permit fluid flow into, but no back flow from, the main passage; and
 e) a resilient gas reservoir attached to the manifold at the collection passage, with the resilient gas reservoir defining a storage chamber therein which is in fluid communication with the collection passage.

22. An apparatus for analyzing a breath gas for a substance, said apparatus comprising:
 a) a gas detector having an inlet port;
 b) a manifold having a body defining a chamber therein, the chamber including a main passage in the manifold body, an outlet passage in fluid communication with the gas detector inlet port and extending into the manifold body toward said main passage, and a metering orifice extending between and in fluid communication with the main passage and an interior end of the outlet passage;
 c) an inlet passage in the manifold body in fluid communication with the main passage;
 d) a collection passage in the manifold body and in fluid communication with the main passage;
 e) a resilient gas reservoir attached to the manifold at the collection passage, with the resilient gas reservoir defining a storage chamber therein which is in fluid communication with the collection passage; and
 f) a check valve in said module between the metering orifice and a free end of the inlet passage opposite the main passage and oriented to permit fluid flow into, but no back flow from, the main passage and the resilient gas reservoir.

23. The breath gas analysis module of claim 22 wherein the check valve is positioned in the inlet passage.

* * * * *

UNITED STATES PATENT AND TRADEMARK OFFICE
CERTIFICATE OF CORRECTION

PATENT NO. : 5,826,577
DATED : October 27, 1998
INVENTOR(S) : William J. Perroz, Jr., et al.

It is certified that error appears in the above-identified patent and that said Letters Patent is hereby corrected as shown below:

Column 5 Line 54 "5,1018,395" should read --5,018,395--.

Claim 1 Column 7 Lines 26-27 after "passage;" delete --tube internal passage and oriented to permit fluid flow into, but--.

Claim 6 Column 7 Line 58 between "the" and "manifold" delete --,--.

Claim 14 Column 8 Line 55 "of claim 12" should read --of claim 13--.

Signed and Sealed this

Thirtieth Day of March, 1999

Attest:

Q. TODD DICKINSON

Attesting Officer

Acting Commissioner of Patents and Trademarks